(12) United States Patent
Coulombe et al.

(10) Patent No.: US 9,308,192 B2
(45) Date of Patent: Apr. 12, 2016

(54) USE OF NRF2 INDUCERS TO TREAT EPIDERMOLYSIS BULLOSA SIMPLEX AND RELATED DISEASES

(71) Applicant: The Johns Hopkins University, Baltimore, MD (US)

(72) Inventors: Pierre A. Coulombe, Laurel, MD (US); Michelle L. Kerns, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 65 days.

(21) Appl. No.: 14/025,485

(22) Filed: Sep. 12, 2013

(65) Prior Publication Data

US 2014/0243267 A1    Aug. 28, 2014

Related U.S. Application Data

(63) Continuation of application No. 12/690,494, filed as application No. PCT/US2008/008694 on Jul. 17, 2008, now abandoned.

(60) Provisional application No. 60/929,985, filed on Jul. 20, 2007.

(51) Int. Cl.
| | |
|---|---|
| *A61K 31/26* | (2006.01) |
| *A61K 31/00* | (2006.01) |
| *A61K 38/18* | (2006.01) |
| *A61K 31/192* | (2006.01) |
| *A61K 31/497* | (2006.01) |

(52) U.S. Cl.
CPC .................. *A61K 31/26* (2013.01); *A61K 31/00* (2013.01); *A61K 31/192* (2013.01); *A61K 31/497* (2013.01); *A61K 38/1825* (2013.01)

(58) Field of Classification Search
None
See application file for complete search history.

(56) References Cited

U.S. PATENT DOCUMENTS

| 5,411,986 A * | 5/1995 | Cho et al. ...................... 514/514 |
| 2011/0014137 A1 * | 1/2011 | Talalay et al. ................... 424/59 |

OTHER PUBLICATIONS

Taylor, Abs. # CHED 722, 231st ACS National meeting, Mar. 26-30, 2006.*
http://www.mayoclinic.org/diseases-conditions/epidermolysis-bullosa/basics/prevention/con-20032497, 1 page, retrieved on Jul. 13, 2015.*
Taylor, Tiffany Natasha et al., "Induction of keratin 17 by sulforaphane, a potent inducer of phase II detoxification enzymes," The 231st ACS National Meeting, 1 page, Poster No. CHED 722 (2006).
Anonymous. Epidermolysis bullosa simplex treated with a chemical from broccoli. Expert Review of Dermatology. Oct. 2007; 2(5):519-521.
Kerns et al. Reprogramming of keratin biosynthesis by sulforaphane restores skin integrity in epidermolysis bullosa simplex. PNAS. Sep. 2007; 104(36):14460-14465.
Zhao et al. Small molecule library screening to identify compounds that regulate keratin 6a expression. J Invest Dermatl. May 2007; 127(1):S94.

* cited by examiner

*Primary Examiner* — Satyanarayana R Gudibande
(74) *Attorney, Agent, or Firm* — Mintz Levin Cohn Ferris Glovsky and Popeo, P.C.; Peter F. Corless, Esq.; Daniel W. Clarke, J.D.

(57) ABSTRACT

The present invention relates to methods and compositions for the prevention and treatment of keratin-based skin diseases. In particular, the application describes compositions and methods of treating a patient suffering from skin blistering comprising the use of phase II enzyme inducers.

47 Claims, 2 Drawing Sheets

Figure 1. Clinical features of Epidermolysis Bullosa Simplex.

*Coulombe / Johns Hopkins University*

```
                  [................head    domain..................
MOUSE  K17  MTTtIRQFTS  SSSIKGSSCL  GGGSSRTSCR  LSGsLGAGSC  R--------- ----------
HUMAN  K17  MTTsIRQFTS  SSSIKGSSUL  GGGSSRTSCR  LSGglGAGSC  R--------- ----------
HUMAN  K14  MTTCSRQFTS  SSSMKGSCGI  GGGIGAGSSR  ISSVLAGGSC  RAPNTYGGGL  SVSSSRFSSG
HUMAN  K16  MATCSRQFTS  SSSMKGSCGI  GGGIGGGSSR  ISSVLAGGSC  RAPSTYGCGL  SVSS-RFSSG
                 +^         ^  ^          ^^^^  ^  ^  ^+  ^^

>>>...........................head   domain................][........
~~~~~~~~~~~  ---------L  GSAsGLGSaL  GsnSYSSCYS  FCtGsGYGgn  FGGVDGLLAG  GEKATMQNLN
~~~~~~~~~~~  ---------L  GSAgGLGStL  GgsSYSSCYS  FGsGgGYGss  FGGVDGLLAG  GEKATMQNLN
GAVGLGGGYG   GGFSSSSSSF  GSGFGGGYGG  GLGAGLGGG-  ------FGGG  FAGGDGLLVG  SEKVTMQNLN
GACGLGGGYG   GGFSSSSS-F  GSGFGGGYGG  GLGAGFGGGL  GAG---FGGG  FAGGDGLLVG  SEKVTMQNLN
                  ^+  ^  ^+^    ++^^^^^^^    ^^+^^  #+      ^   ^   ^

...1A domain..............]                 [........1B domain........
DRLASYLDKV  RALEEANTEL  EVKIRDWYQk  QAPGPARDYS  aYYhTIEdLk  NKILvATVDN  AsILLQIDNA
DRLASYLDKV  RALEEANTEL  EVKIRDWYQr  QAPGPARDYS  qYYrTIEeLq  NKILtATVDN  AnILLQIDNA
DRLASYLDKV  RALEEANADL  EVKIRDWYQR  QRPAEIKDYS  PYFKTIEDLR  NKILTATVDN  ANVLLQIDNA
DRLASYLDKV  RALEEANADL  EVKIRDWYQR  QRPSKIKDYS  PYFKTIEDLR  NKIlAATIEN  AQPILQIDNA
                ^^         +    ^  ^^^^        +  ^-   #  +      +     +^

>>>..............................................................]
RLAADDFRTK  FETEQALRmS  VEADINGLRR  VLDELTLARA  DLEMQIENLK  EELAYLKKNH  EEEMNALRGQ
RLAADDFRTK  FETEQALRlS  VEADINGLRR  VLDELTLARA  DLEMQIENLK  EELAYLKKNH  EEEMNALRGQ
RLAADDFRTK  YETELNLRMS  VEADINGLRR  VLDELTLARA  DLEMQIESLK  EELAYLKKNH  EEEMNALRGQ
RLAADDFRTK  YEHELALRQT  VEADVNGLRR  VLDELTLART  DLEMQIEGLK  EELAYLRKNH  EEEMLALRGQ
                 ^    #                ^

[.............2A domain.............]        [...
VGGEINVEMD  AAPGVDLSRI  LsEMRDQYEK  MAEKNRKDAE  DWFFSKTEEL  NREVATNSEL  VQSGKSEISE
VGGEINVEMD  AAPGVDLSRI  LnEMRDQYEK  MAEKNRKDAE  DWFFSKTEEL  NREVATNSEL  VQSGKSEISE
VGGDVNVEMD  AAPGVDLSRI  LNEMRDQYEK  MAEKNRKDAE  SWFFTKTEEL  NREVATNSEL  VQSGKSEISN
TGGDVNVEMD  AAPGVDLSRI  LNEMRDQYEQ  MAEKNRRDAE  TWFLSKTEEL  NKEVASNSEL  VQSSRSEVTE
                              +           ^

>>>>........................................2B domain............
LRRTMQALEI  ELQSQLSMKA  SLEGsLAETE  NRYCVQLSQI  QGLIGSVEEQ  LAQLRCEMEQ  QNQEYKILLD
LRRTMQALEI  ELQSQLSMKA  SLEGnLAETE  NRYCVQLSQI  QGLIGSVEEQ  LAQLRCEMEQ  QNQEYKILLD
LRRTMQNLEI  ELQSQLSMKA  SLENSLEETK  GRYCMQLAQI  QEMIGSVEEQ  LAQLRCEMEQ  QNQEYKILLD
LRRVLQGLEI  ELQSQLSMKA  SLENSLEETK  GRYCMQLSQI  QGLIGSVEEQ  LAQLRCEMEQ  QSQEYQILLD
    ^                     ^+  ^ ^    ^

........................][...................tail   domain...........
VKTRLEQEIA  TYRRLLEGED  AHLTQYKpKE  P--------V  TT-----RQV  RTIVEEVQDG  KVISSREQVH
VKTRLEQEIA  TYRRLLEGED  AILTQYK-KE  P--------V  TT-----RQV  RTIVEEVQDG  KVISSREQVH
VKTRLEQEIA  TYRRLLEGED  AHLSSSGFSS  GSQSSRDV-T  SSS-----RQI  RTKVMDVHDG  KVVSTHEQVL
VKTRLEQEIA  TYRRLLEGED  AHLSSQQASG  QSYSSREVFT  SSSSSSSRQT  RPILKEQSSS  SFSGQSS*
                 ^^^^+^^  ^         ^   ^^         ###^##^##  ##^#^^^#

...]
QTTR*
QPTR*
RTKN*
^ ^^
```

Figure 2. Alignment of K17, K16 and K14 protein sequences.
(Source: McGowan and Coulombe, J. Cell Biol. 1998)

USE OF NRF2 INDUCERS TO TREAT EPIDERMOLYSIS BULLOSA SIMPLEX AND RELATED DISEASES

CROSS-REFERENCE TO RELATED APPLICATIONS

This application is a continuation application of U.S.S.N.12/690,494, filed Jan. 20, 2010, which is a national stage application filed under 35 U.S.C. §of international application no. PCT/US2008/08694, filed Jul. 17, 2008, which claims the benefit of U.S. Provisional Application No. 60/929,985, filed Jul. 20, 2007, the contents of each of which are incorporated by reference in their entireties.

CROSS- REFERENCE TO RELATED APPLICATIONS

This application claims the benefit U.S. Provisional Application No. 60/929,985.

SEQUENCE LISTING

The instant application contains a Sequence Listing which has been submitted electronically in ASCII format and is hereby incorporated by reference in its entirety. Said ASCII copy, created on Dec. 3, 2013, is named 85531CON (71699)_SL.txt and is 16,083 bytes in size.

BACKGROUND OF THE INVENTION

The skin is continuously exposed to changes in the external environment, including oxidative insults, heat, cold, UV radiation, injury, and mechanical stresses. The stratum corneum, composed of terminally differentiated keratinocytes, constitutes the natural barrier that prevents loss of water and prevents entry of infectious agents (e.g., bacteria, viruses), small objects (e.g., particles), and a broad variety of water-soluble chemicals.

Intermediate filaments (IFs), microtubules (MTs) and microfilaments (MFs) constitute the cytoskeleton and play important roles in the organization and mechanical Integrity of skin keratinocytes (Fuchs and Cleveland, 1998). Keratins are a large family of proteins that form the intermediate filament cytoskeleton in epithelial cells. Keratins are encoded by two groups of genes, type I and II, which are distinct at the level of genomic structure and nucleotide sequence. Each type of keratin gene is clustered within separate loci in the mouse and human genomes (Fuchs, 1995; Schweizer at al., 2006). Type II keratin proteins, which include K1-K8/K71-K74 in soft epithelia and K81-K86 in hard epithelia, such as hair, nail, and oral papilla, are larger (52 to 70 kDa) and basic-neutral in charge; type I keratins, which comprise K9-K28 in soft epithelia and K31-K40 in hard epithelia, are smaller (40 to 64 kDa) and acidic (Schweizer et al., 2006). The physical proximity, identical substructure and transcriptional orientation, and high sequence homology of type II keratin genes K5, K6α, K6β and K6hf, and type I keratin genes K14, K16, K17 and K17n, strongly suggest that each subset was generated through successive duplications from a common ancestral gone (Wong at al., 2005). Type I epidermal keratin genes K14, K16 and K17 share high amino acid sequence identity (Troyanovsky et al., 1992; McGowan and Coulombe, 1998; 1998b), and are structurally and functionally related (Paladini and Coulombe, 1999; Coulombe et al., 2004; Tong and Coulombe, 2006).

In most epithelial cells the keratin filament network spans the entire cytoplasm, from the surface of the nucleus to the cell periphery, where it contacts cell-matrix (hemidesmosomes) and cell-cell (desmosomes) adhesive sites (e.g., Fuchs, 1995; Gu and Coulombe, 2007). Keratin Intermediate filaments provide cells and tissues with mechanical resilience and protects them against physical stress. Disruption of the keratin scaffold leads to tissue and cell fragility in the skin and its appendages (hair, nail, glands), oral mucosa, and cornea. Several genetic diseases are caused by dominantly-acting mutations altering the coding sequence of keratin proteins (Fuchs and Cleveland, 1998; On and Coulombe, 2007; Irvine and McLean, 1999; Omary et al., 2004). Most of these mutations are missense or small in-frame insertions or deletions affecting the central rod domain of keratin proteins, and interfering with their structural support function (Cassidy et al. 2002; Gu and Coulombe 2007).

Epidermolysis bullosa simplex (BBS) is a rare autosomal dominant disease in which the epidermis loses its integrity following trivial mechanical trauma (Fine at al., 1991; 2000). The disease is characterized by extreme fragility of the keratinocytes, and skin blistering, resulting from missense mutations in the gene that encodes keratin 5 (K5) or keratin 14 (K14) (Fuchs and Cleveland, 1998; Cassidy at al. 2002; Gu and Coulombs 2007; Omary et al., 2004). K5 and K14, which are abundant cellular proteins, normally co-polymerize to form an intricate network of 10-12 nm-wide, "intermediate-sized" filaments in basal keratinocytes of epidermis and related epithelia (Nelson and Sun, 1983; Fuchs, 1995). EBS may manifest itself as a relatively mild blistering condition involving the hands and feet (EBS, Weber-Cockayne type), or as a generalized blistering condition, sometimes associated with mucosal blistering that involves the oropharynx, the esophagus and ocular mucosa, and which can be fatal (e.g., EBS, Dowling-Meara type). In individuals affected by EBS Weber-Cockayne (EBS-WC), blisters are rarely present at birth and may occur on the knees and shins with crawling, or on the feet in late infancy or later, during adolescence or early adulthood. Neonates affected by EBS, Koebner type (EBS-K), present blisters at birth or develop blisters within the first few months of life (Fine at al., 1991; 2000). In individuals suffering from EBS with mottled pigmentation (EBS-MP), skin fragility is evident at birth and children develop progressive brown pigmentation over time, interspersed with depigmented spots on the trunk and extremities, which disappears in adult life (see Gu and Coulombs, 2007, and refs. therein). Individuals affected by BBS-DM develop widespread and severe blistering and/or multiple grouped clumps of small blisters at birth, with hyperkeratosis of the palms and soles, that improves during mid to late childhood. The blistering in EBS-DM can be severe enough to result in neonatal or infant death (Fine at al., 2000).

Management of all types of EBS consists of supportive care to protect the skin from blistering, dressings that promotes healing, and prevention and treatment of secondary infection. These treatment options are therefore palliative and have limited success. Furthermore, EBS is representative of a large number of tissue fragility conditions caused by inherited mutations in intermediate filament protein-encoding genes (sue Fuchs and Cleveland, 1998; Cassidy at al., 2002; Omary et al., 2004; Gu and Coulombs, 2007).

Accordingly, there is a need in the art for improved treatment options for EBS and the present invention satisfies that need.

SUMMARY OF THE INVENTION

It is, therefore, an object of the invention to provide solutions to the aforementioned deficiencies in the art.

Further to this object, the invention provides a method to ameliorate the compromised state of mechanical resilience of skin in a patient comprising administering to the patient a composition comprising a therapeutically effective amount of an Nrf2 inducer. The patient to be treated may suffer from skin blistering. In one aspect of the invention, the patient may be affected by Epidermolysis bullosa simplex. In a preferred embodiment of the invention, the patient suffers from Epidermolysis bullosa simplex-Weber-Cockayne type, Epidermolysis bullosa simplex-Koebner type, Epidermolysis bullosa simplex with mottled pigmentation, Epidermolysis bullosa simplex-Dowling-Meara type, or Epidermolysis bullosa simplex with muscular dystrophy.

In a further embodiment, the method to ameliorate the mechanical resistance of the skin comprises administering a phase II enzyme inducer. In one embodiment, the phase II inducer is an isothiocyanate. In a preferred embodiment the phase II enzyme inducer is sulforaphane. In another preferred embodiment, the phase II enzyme inducer is a sulforaphane synthetic analogue. In yet another embodiment, the Nrf2 inducer is keratinocyte growth factor, also known as fibroblast growth actor 7. In an additional embodiment, the Nrf2 inducer is oltipraz. In a further embodiment, the Nrf2 inducer is ethacrynic acid. In still another preferred embodiment, the Nrf2 inducer causes the selective induction of K6, K16 or K17 in the keratinocytes in the skin of the patient.

In an additional embodiment, the present invention provides a method for treating or preventing skin blistering in a patient comprising administering to the patient a composition comprising a therapeutically effective amount of an Nrf2 inducer. In one aspect of the invention, the patient may be affected by Epidermolysis bullosa simplex. In a preferred embodiment of the invention, the patient suffers from Epidermolysis bullosa simplex-Weber-Cockayne type, Epidermolysis bullosa simplex-Koebner type, Epidermolysis bullosa simplex with mottled pigmentation, Epidermolysis bullosa simplex-Dowling-Meara type, or Epidermolysis bullosa simplex with muscular dystrophy.

In a further embodiment, the method for treating or preventing skin blistering comprises administering a phase II enzyme inducer. In one embodiment, the phase II inducer is an isothiocyanate. In a preferred embodiment the phase II enzyme inducer is sulforaphane. In another preferred embodiment, the phase II enzyme inducer is a sulforaphane synthetic analogue. In yet another embodiment, the Nrf2 inducer is keratinocyte growth factor. In an additional embodiment, the Nrf2 inducer is oltipraz. In a further embodiment, the Nrf2 inducer is ethacrynic acid. In a further embodiment, the Nrf2 inducer is a Michael reaction acceptor, such as triterpenoids or cyclic/acyclic bis-benzylidene-alkalones. In still another preferred embodiment, the Nrf2 inducer causes the selective induction of K6, K16 or K17 in the keratinocytes in the skin of the patient.

In yet another embodiment, the present invention provides a method for treating or preventing a keratin-based skin disease in a patient comprising administering to the patient a composition comprising a therapeutically effective amount of an Nrf2 inducer. The patient to be treated may be affected by an epidermolytic or non-epidermolytic keratin-based skin disease. Exemplary types of keratin-based skin diseases (Cassidy at al., 2002) to be treated include, but are not limited to, epidermolytic hyperkeratosis, ichtyosis bullosa of Siemens, pachyonychia congenita, epidermolytic or non-epidermolytic palmoplantar keratoderma (diffuse or focal) steatocystoma multiplex, Naegeli-Franceschetti-Jadassohn syndrome and dermatopathia pigmentosa reticularis. In one embodiment, the keratin-based skin disease is caused by a mutation at the K14 locus.

In a further embodiment, the method for treating or preventing a keratin-based skin disease comprises administering a phase II enzyme inducer. In one embodiment, the phase II enzyme inducer. In a preferred embodiment the phase II enzyme inducer is sulforaphane. In another preferred embodiment, the phase II enzyme inducer is a sulforaphane synthetic analogue. In yet another embodiment, the Nrf2 inducer is keratinocyte growth factor. In an additional embodiment, the Nrf2 inducer is oltipraz. In a further embodiment, the Nrf2 inducer is ethacrynic acid. In a further embodiment, the Nrf2 inducer is a Michael reaction acceptor, such as triterpenoids or cyclic/acyclic bis-benzylidene-alkalones. In still another preferred embodiment, the Nrf2 inducer causes the selective induction of K6, K16 or K17 in the keratinocytes in the skin of the patient.

In an additional embodiment, the present invention provides a composition for topical application to the skin comprising a therapeutically effective amount of an Nrf2 inducer and a vehicle suitable for delivery. Topical compositions may be in several forms, such as solutions, oils, creams, ointments, gels, lotions, or pastes, and include, for instance, the penetration enhancer "transcutanol" (diethylene glycol monoethylether), or other excipients well known in the art.

Preferably, the Nrf2 inducer in the composition is a phase II enzyme inducer. More preferably, the phase II inducer is an isothiocyanate. Even more preferably, the phase II enzyme inducer is sulforaphane or a sulforaphane synthetic analogue. In another embodiment, the Nrf2 inducer is keratinocyte growth factor. In yet another embodiment, the Nrf2 inducer is oltipraz. In a further embodiment, the Nrf2 inducer is ethacrynic acid. In a further embodiment, the Nrf2 inducer is a Michael reaction acceptor, such as triterpenoids or cyclic/acyclic bis-benzylidene-alkalones. In a preferred embodiment, the Nrf2 inducer causes the selective induction of K6, K16 or K17 in the keratinocytes in the skin of the patient.

The Nrf2 inducer in the composition of the invention may be administered alone or in combination with additional active agents, including pharmaceutical, biological and/or molecular biological active agents in the context of combination or adjuvant therapy.

The foregoing general description and following brief description of the drawings and the detailed description are exemplary and explanatory and, along with the manuscript appended, are intended to provide further explanation of the invention as claimed. Other objects, advantages, and novel features will be readily apparent to those skilled in the art from the following detailed description of the invention.

BRIEF DESCRIPTION OF THE DRAWINGS

FIG. 1 illustrates the clinical features of Epidermolysis bullosa simplex in a 2-month old baby girl born prematurely. The patient had recurrent bullae from shortly after birth, particularly in trauma-prone areas. The blisters typically healed with hypopigmentation as new lesions formed. The patient's father bad similar lesions as a newborn and complained of recurrent bullae on his hands and feet. FIG. 1A shows the presence of several skin erosions at various stages of healing in the abdomen and upper thighs (the source of frictional trauma in the upper thighs is the diaper). FIG. 1B details the presence of several large fluid-filled blisters on the dorsal and lateral sides of toes and heel (depicted by single arrows and double arrows, respectively). Some of the toenails are also affected. The prominent soft bandage wrapped around the distal portion of the right foot is an attempt to prevent further trauma to the toes.

FIG. 2 illustrates the alignment of the predicted amino acid sequences for mouse K17 (SEQ ID NO: 1) and human K17 (SEQ ID NO: 2), K14 (SEQ ID NO: 3)and K16(SEQ ID NO: 4). This alignment was produced using the DNASIS v.3.5 software (Hitachi Software Engineering Inc., Japan). Default parameters were applied. The boundaries of the major domains recognized in all IF proteins (Fuchs and Weber, 1994) are depicted with brackets: the non-helical head domain at the N-terminus; the α-helical subdomains 1A, 1B, 2A, and 2B characteristic of the central rod domain; and the non-helical tail domain at the C-terminus. Nonsense stop codons are depicted by asterisks. Both symbols "+" and "#" underneath the sequences identify residues that are different between mouse and human K17. The symbol "#" marks the subset for which mouse K17 is identical to either K14 or K16; the symbol "^" identifies residues that are conserved between mouse and human K17, but different from K14 and K16.

DETAILED DESCRIPTION OF THE INVENTION

Transcription factor NF-E2-related factor 2 (Nrf2) belongs to the CNC (Cap-N-Collar) family of transcription factors and possesses a highly conserved basic region-leucine zipper (bZip) structure. Nrf2 plays a critical role in the constitutive and inducible expression of anti-oxidant and detoxification genes, commonly known as phase II genes, that encode defensive enzymes, including drug metabolizing enzymes, such as glutathione S-transferase, NADP(H):quinone oxidoreductase and UDP-glucuronosyltransferase, and anti-oxidant enzymes, such as heme oxygenase-1-(HO-1)1 and γ-glutamylcysteine synthetase (GCS), in response to oxidative and xenobiotic stress (Braun et al., 2002; Fahey at al., 1997; Fahey and Talalay, 1999; Holtzclaw et al., 2004; Motohashi and Yamamoto, 2004). These enzymes are regulated through a promoter called anti-oxidant responsive element (ARE) or electrophile response element (EpRE). Phase II genes are responsible for cellular defense mechanisms that include the scavenging of reactive oxygen or nitrogen species (ROS or RNS), detoxification of electrophiles and maintenance of intracellular reducing potential (Holtzclaw et al., 2004; Motohashi and Yamamoto, 2004).

Nrf2 is normally sequestered in the cytoplasm of the cells by an actin-bound regulatory protein called Keap1. When cells are exposed to oxidative or electrophilic stress, the Keap1-Nrf2 complex undergoes a conformational change, and Nrf2 is liberated from the complex and released into the nucleus. The active Nrf2 dimerizes with small Maf proteins, binds to ARE and activates phase II gene transcription (Braun et al., 2002; Motohashi and Yamamoto, 2004).

There is increasing evidence that the induction of phase II enzymes protects from carcinogenesis and mutagenesis and enhances the antioxidant capability of the cells (Fahey and Talalay, 1999; Iida et al., 2004). To date, nine classes of phase II enzyme inducers have been identified: 1) diphenols, phenylene diamines and quinones; 2) Michael acceptors; 3) isothiocyanates; 4) hydroperoxides and hydrogen peroxide; 5) 1,2-dithiole-3-thiones; 6) dimercaptans; 7) trivalent arsenicals; 8) divalent heavy metals; and 9) carotenoids, curcumins and related polyenes (Fahey and Talalay, 1999). These phase II enzyme inducers are considered very efficient antioxidants because unlike direct antioxidants, they are not consumed stoichiometrically during oxide-reduction reactions, have long duration of action, support the function of direct antioxidants, such as tocopherols and CoQ, and enhance the synthesis of glutathione, a strong antioxidant (Fahey and Talalay, 1999).

The diuretic ethacrynic acid (EA), an electrophilic Michael acceptor, oltipraz, and the isothiocyanate sulforaphane have been shown to inhibit lipopolysaccharide (LPS)-induced secretion of high-mobility group box 1 (HMGB1), a proinflammatory protein implicated in the pathogenesis of inflammatory diseases, from immunostimulated macrophages (Killeen at al., 2006). Oltipraz prevents carcinogenesis in liver and urinary bladder by enhancing carcinogen detoxification (Iida at al., 2004). The cytoprotective effect of keratinocyte growth factor (KGF) against oxidative stress in injured and inflamed tissues, including wounded skin, has been related to KGF's stimulation of Nrf2 during cutaneous wound repair (Braun et al., 2002).

Isothiocyanates, which are primarily derived from in cruciferous vegetables, are potent antioxidants and effective agents in the chemoprevention of tumors via the activation of phase II enzymes, inhibition of carcinogen-activating phase I enzymes and induction of apoptosis (Hecht, 1995; Zhang and Talalay, 1994; Zhang et al., 1994). Isothiocyanates are formed in plants from the hydrolysis of glucosinolates, which are β-thioglucoside-N-hydroxysulfates, when maceration of the vegetables by predators, food preparation or chewing causes disruption of the calls with consequent activation and release of the enzyme myrosinase. The resultant aglycones undergo non-enzymatic intramolecular rearrangement to yield isothiocyanates, nitriles and epithionitriles.

Sulforaphane is the aglycone breakdown product of the glucosinolate glucoraphanin, also known as sulforaphane glucosinolate (SOS). The molecular formula of sulforaphane is $C_6H_{11}NOS_2$, and its molecular weight is 177.29 daltons. Sulforaphane is also known as 4-methylsulfinylbutyl isothiocyanate and (−)-1-isothiocyanato-4(R)-(methylsulfinyl)butane. The structural formula of sulforaphane is:

Sulforaphane was first synthesized (Schmid and Karrer, 1945), and then isolated from the weed hoary cress (*Cardaria draba*), savoy and red cabbage (Prochazka, 1959). More recently, sulforaphane was identified in broccoli and shown to be a potent phase II enzyme inducer in isolated murine hepatoma cells (Zhang et al., 1992), block the formation of mammary tumors in Sprague-Dawley rats (Zhang at al.; 1994), prevent promotion of mouse skin tumorigenesis (Gills at al., 2006; Xu et al., 2006) and increase heme oxygenase-1 (HO-1) expression in human hepatoma HepC2 cells (Keum et al., 2006). Sulforaphane was also shown to inhibit ultraviolet (UV) light-induced activation of the activator protein-1 (AP-1), a promoter of skin carcinogenesis, in human keratinocytes (Zhu et al., 2004), and there is evidence that topical application of sulforaphane extract increases the level of phase II enzymes NAD(P)H:quinone oxidoreductase I (NQO1), glutathione S-transferase A1 and heme oxygenase 1 in mouse skin epidermis (Dinkova-Kostova et al., 2007). Moreover, sulforaphane protects human epidermal keratinocytes against sulfur mustard, a potent cytotoxic agent and powerful mutagen and carcinogen (Gross of al., 2006), and inhibits cell growth, activates apoptosis, inhibits histone deacetylase (HDAC) activity and decreases the expression of estrogen receptor-α, epidermal growth factor receptor and human epidermal growth factor receptor-2, which are key proteins involved in breast cancer proliferation, in human breast cancer cells (Pledgie-Tracy et al., 2007). Further, sulforaphane was showed to eradicate *Helicobacter pylori* from human gastric xenografts (Haristoy et al., 2003).

The present inventors discovered that topical application of Nrf2 inducers to the skin markedly improve the mechanical resilience of skin and prevents or reduce skin blistering in mammals, and specifically in human subjects suffering from a keratin-based skin disease, particularly a skin disease caused by a mutation at the K14 locus, thanks to their ability to trigger ectopic expression of structurally- and functionally-related keratins in basal layer keratinocytes.

Type 1 epidermal keratins K14, K16, and K17 are remarkably similar at the primary sequence level (see FIG. 2). There is direct and indirect evidence in the literature indicating that K14, K16, and K17 are redundant to a significant extent in their ability to foster structural support in stratified epithelia such as epidermis. There also is evidence that K17 fulfills two additional functions, likely in a context-dependent fashion, in skin epithelia. The first function is the protection against TNFalpha-induced programmed cell death, which is shared with K14 and K16 (Tong and Coulombe, 2006). The second function is stimulation of protein synthesis and epithelial cell growth, which is so far unique to K17 and restricted to the wound repair response (Kim et al., 2006). These two roles would be expected to be either neutral, or beneficial, in the context of EBS treatment. It has also been proposed that K16 plays a role in the process of keratinocyte activation that occurs after acute injury to the stratified epithelia (Paladini et al., 1996; Paladini and Coulombe, 1998; 1999). Since the structural support function of keratins is defective in EBBS and related conditions, accumulation of "surrogate" keratins (e.g., K16, K17) can "dilute away", or attenuate, the dominant negative impact of the mutant protein (e.g., K14) responsible for the disease (Cao et al., 2001; Kerns et al.).

The inventors of the present application have made the discovery that treatment with sulforaphane (SF), a chemical naturally present in the diet, significantly decreases the massive skin blistering seen in a mouse model of EBS, thanks to sulforaphane's ability to selectively induce keratin genes whose structural support function is markedly redundant with K14. These genes are K16 and K17 (see Paladini and Coulombe, 1999; McGowan et al., 2002; Coulombe et al., 2004; Tong and Coulombe, 2006) (FIG. 2). In contrast to its clear impact on K16 and K17 expression, SF is not effective at inducing other relevant keratins in the epidermis, including K5, or K14, and has a weaker impact on K6 expression (Kerns et al.). The key aspect of SF's efficacy in treating EBS consists in its ability to cause activation of K16 and K17 expression in basal keratinocytes of epidermis. However, the mechanism by which sulforaphane causes induction of select keratins in treated skins is not known.

Our studies have shown that sulforaphane's effect does not reach the basal layer of epidermis, a key requirement for EBS therapy, when dissolved in an organic solvent like acetonitrile or acetone (date not shown). In contrast, sulforaphane impacts gene expression in the desired manner in basal keratinocytes of mouse epidermis when topically administered in select formulations that comprise a carrier, such as, but not limited to, jojoba oil and evening primrose oil, that allows sulforaphane to reach basal keratinocytes in the epidermis. These formulations may be modified according to various factors affecting human akin, including the age of the subject being treated and the site of treatment in the body.

The terms "subject" and "patient" are used interchangeably and are meant to refer to an animal. In a preferred aspect of the invention, the patient is a mammal. In the most preferred aspect of the Invention, the mammal is a human. Other suitable subjects or patients include, but are not limited to, laboratory animals, such as mouse, rat, rabbit or guinea pigs, farm animals and domestic animals or pets.

An epidermolytic or a non-epidermolytic keratin-based skin disease, as used in the current context, should be obvious to the person skilled in the art, and is meant to include any abnormality in the skin, where a keratin gene mutation is involved in the etiology of the disorder or is affected by the disorder. Examples of epidermolytic or a non-epidermolytic keratin-based skin diseases for which the current invention could be used preferably include, but are not limited to, epidermolysis bullosa simplex, epidermolytic hyperkeratosis, ichtyosis bullosa of Siemens, pachyonychia congenita, epidermolytic or non-epidermolytic palmoplantar keratoderma (diffuse or focal) steatocystoma multiplex, Naegeli-Franceschetti-Jadassohn syndrome and dermatopathia pigmentosa reticularis.

The treatment envisioned by the invention can be used for patients with a pre-existing condition, or for patients pre-disposed to a keratin-based skin disease. Additionally, the methods of the invention can be used to alleviate symptoms of keratin-based skin disease in patients, or as a preventative measure in patients. Finally, the treatment envisioned could also be used as a complement to other agents in the context of a combination or adjuvant therapy for administration to a subject that is being treated with one or more conventional drugs. Such drugs can be administered concurrently with, prior to or sequentially with Nrf2 inducer or phase II enzyme inducer treatment.

As used herein, "a pharmaceutically effective amount" is intended to mean an amount effective to elicit a cellular response that is clinically significant.

The present invention relates to methods of preventing or treating EBS and other keratin-based skin diseases using phase II enzyme inducers as described above.

Isothiocyanates are compounds containing the isothiocyanate (NCS) moiety and are easily identifiable by one of ordinary skill in the art. An example of an isothiocyanate includes, but is not limited to sulforaphane or its analogs. The description and preparation of isothiocyanate analogs is described in U.S. Reissue Pat. No. 36,784, and is hereby incorporated by reference in its entirety. The sulforaphane analogs used in the present invention include 6-isothiocyanato-2-hexanone, exo-2-acetyl-6-isothiocyanatonorbornane, exo-2-isothiocyanato-6-methylsulfonyinorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanate and trans-3-(methylsulfonyl)cyclohexylmethylisothiocyanate.

Other compounds contemplated by the present invention include keratinocyte growth factor (KGF), oltipraz, ethacrynic acid, and analogs thereof, as well a additional Michael reaction acceptors, such as triterpenoids or cyclic/acyclic bis-benzylidene-alkalenes.

The compounds used in the methods of the present invention can be formulated into pharmaceutical compositions with suitable, pharmaceutically acceptable excipients for topical administration to mammals. Such excipients are well known in the art. Topical administration includes administration to the skin or mucosa, including surfaces of the lung and eye.

Dosage forms for topical administration include, but are not limited to, ointments, creams, emulsions, lotions and gels and agents that favor penetration within the epidermis. In a preferred embodiment, the composition is in the form of topical ointment.

The compounds of the invention may be administered alone or in combination with additional active agents, including pharmaceutical, biological and/or molecular biological active agents in the context of combination or adjuvant therapy. The compositions can also contain adjuvants such as, but not limited to, solubilizers, skin permeation enhancers, preservatives, wetting agents, moisturizers, gelling agents, buffering agents, surfactants, emulsifying agents, emollients, thickening agents, stabilizers, humectants and dispersing agents.

Moisturizers include carriers that allow the Nrf2 inducer or phase II enzyme inducer to reach basal keratinocytes in the epidermis. This may be achieved by varying the formulation according to several factors affecting human skin, including the age of the subject being treated and the body site. Examples of moisturizers include, but are not limited to, jojoba oil and evening primrose oil.

Suitable skin permeation enhancers are well known in the art and include lower alkanols, such as methanol ethanol and 2-propanol; alkyl methyl sulfoxides such as dimethylsulfoxide (DMSO), decylmethylsulfoxide ($C_{10}$ MSO) and tetradecylmethyl sulfoxide; pyrrolidones, urea; N,N-diethyl-m-toluamide; $C_2$-$C_6$ alkanediols; dimethyl formamide (DMF), N,N-dimethylacetamide (DMA) and tetrahydrofurfuryl alcohol.

Examples of solubilizers include, but are not limited to, hydrophilic ethers such as diethylene glycol monoethyl ether (ethoxydiglycol, available commercially as Transcutol®) and diethylene glycol monoethyl ether oleate (available commercially as Softcutol®); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol®); alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the compositions of the invention.

One of ordinary skill will appreciate that effective amounts of the agents in the compositions used in the methods of the Invention can be determined empirically. It will be understood that, when administered to a human patient, the total daily usage of the composition of the present invention will be decided by the attending physician within the scope of sound medical judgment. The specific therapeutically effective dose level for any particular patient will depend upon a variety of factors: the type and degree of the response to be achieved; the activity of the specific composition employed; the age, body weight, general health, sex and diet of the patient; the duration of the treatment; drugs used in combination or coincidental with the method of the invention; and like factors well known in the medical arts.

Typically, the amount of Nrf2 inducer in the composition topically administered to the patient will be from about 100 nmol to about 1 μmol/cm², and the composition will be applied directly on the skin over relevant portions of the body of the patient two or three times a week, so as to prevent or minimize blistering resulting from frictional trauma.

EXAMPLES

Source of Sulforaphane

Pure sulforaphane (SF) was used in our studies (Zhang et al., 1992).

Example 1

K14 Null and K5 Null Mouse Strains as Models for Very Severe EBS Disease

Introduction of null mutations at the K14 locus (Lloyd et al., 1995) and K5 locus (Peters et al., 2001) in mice essentially abrogate the keratin filament network in basal keratinocytes in the epidermis, and renders the keratinocytes acutely fragile in the face of physiological levels of mechanical trauma. The presence of small amounts of K15, a type I keratin related to K14, leaves a residual but wispy keratin filament network in basal keratinocytes of K14 null epidermis. Accordingly, K5 null mice show more extensive skin blistering and die sooner (before P0.5) than K14 null mice (P2-P3 in K14 null mice). Thus, these two mouse models represent very severe forms of the disease.

Figure 1:
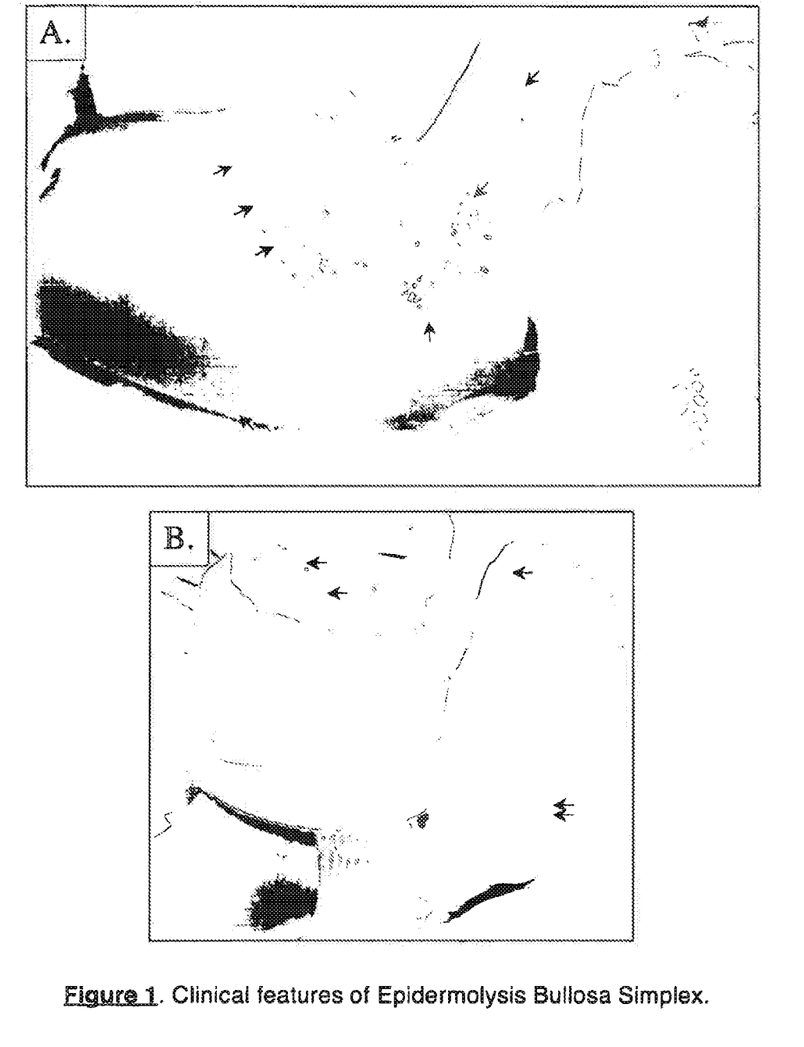

The K14 null mouse strain (Lloyd at al., 1995) has proven to be the more useful model for these studies. The selective fragility of epidermal basal cells and the associated trauma-induced skin blistering seen in K14-null mice mimics EBS as seen in humans. This said, this mouse model presents unique challenges that are relevant only to a small subset of human EBS patients (FIG. 1). The main challenge is premature death, which is largely due to extensive oral blistering and its acute impact on the feeding, stamina, and growth of newborn pups. Beginning shortly after birth, K14 null mice become fragile, lethargic, and can be distinguished from their "normal" littermates ($K14^{+/+}$ or $K14^{+/-}$). By P2, K14 null pups are significantly smaller, lack milk in their bellies, and are unable to close their mouths, correlating with local swelling. At P0 and P2, their lips and tongue exhibit very severe epithelial blistering. In our hands, the mean survival of the K14-null mice is 2.5±0.35 days (n=14, p<0.01). Oral lesions are only seen occasionally in newborns afflicted with EBS (Fine et al., 1991; see also FIG. 1B). The K14 null mouse strain thus provides a very stringent test for the notion that treatment with SF could be effective in the therapeutic management of skin blistering in EBS patients.

Example 2

Ectopic Expression of GB2 Rescues Skin Blistering in K14 Null Mice but not in K5 Null Mice Keratin 17 is a direct target for the transcription factor Gli2, a powerful terminal effector of hedgehog signaling pathways (Bianchi et al., 2005). In $Gli2^{TG}$ transgenic mice (Grachtehouk et al., 2000), expression of the Gli2 coding sequence is controlled by the K5 gene promoter, thereby causing its accumulation in the basal layer of epidermis. $Gli2^{TG}$ mice appear normal at birth and in the days thereafter, but they develop epidermal hyperplasia as young adults, which progresses to basal cell carcinoma by 2-3 months of age. Availability of $Gli2^{TG}$ transgenic mice provided an opportunity to conduct a "proof of principle" experiment, whereby constitutive expression of $Gli2^{TG}$ transgene in the setting of $K14^{-/-}$ mice should cause a stable upregulation of K17 in basal keratinocytes of epidermis, and hence, rescue their oral and skin blistering. Conversely, the Gli2$^{TG}$ transgene should not rescue the phenotype arising in K5 null mice, given that Gli2 has a very modest impact on type II keratin gene regulation in epidermis (see Kerns et al.).

Gli2$^{TG}$ transgenic mice were thus mated with K14 null mice, and the resulting offsprings analyzed for readouts relevant to the K14 null mutation. Unlike their K14$^{-/-}$ littermates, the K14$^{-/-}$ Gli2$^{TG}$ mice were initially viable and showed normal skin, correlating with the presence of K17 in basal cells. This was in contrast to K5$^{-/-}$ Gli2$^{TG}$ mice, which died shortly after birth, exactly as straight K5 null mice did. These findings strongly suggest that rescue of an EBS-like condition can be achieved by exploiting functional redundancy within the keratin multigene family, and the presence or activation of a relevant transcription factor in basal keratinocytes can ectopically induce a keratin gene without affecting epidermal physiology.

Example 3

Sulforaphane Selectively Induces K16 and K17 in Skin Keratinocytes In Vitro and In Vivo To evaluate the effect of sulforaphane (SF) on keratin gene transcription in vitro, a mouse keratinocyte line (308 cells) was exposed to 1 µM SF in acetonitrile vehicle, and mRNA levels were measured at 12, 24, and 48 hours after treatment. Relative to vehicle treatment, SF-treated keratinocytes showed a significant increase in the mRNA levels of NQO1, a well-established SF target, at all time points as expected (Dinkova-Kostova, et al., 2006). Similarly to NQO1, K17 and K16 mRNAs were each elevated ~2.5 fold at 12 h after SF treatment, but their induction was shorter-lived and levels returned to baseline by 24 hours. No significant change was measured for K5, K6a, K6b, K14 and K15 mRNA levels. Indirect immunofluorescence revealed an obvious induction of K17, but not K14, at the protein level.

At higher doses and in some specific contexts, SF induces apoptosis, or programmed cell death (Gamet-Payrestre et al., 2000; Fimongnari et al., 2002; Misiewicz et al., 2003; Gingras, et al., 2004). However, in the experiments described above, SF did not alter the intrinsically low rate of apoptosis seen in primary cultures of mouse keratinocytes, when present at a 1 µM concentration in the culture medium. At higher concentrations (5 µM), SF did alter the rate of apoptosis (16% in control treated-cells versus 94% in SF-treated cells). Thus, at a dose sufficient to alter keratin gene expression in a selective fashion (1 µM), SF does not cause apoptosis in cultured primary mouse keratinocytes.

To uncover whether SF had a similar effect on keratin expression in vivo and after sustained treatment, SKH-1 hairless mice were topically treated with 1 µmole SF in jojoba oil, a vehicle that readily penetrates the skin (El Laithy and El-Shaboury, 2002), twice a week for four weeks. Compared to vehicle-treated skin, SF-treated skin showed markedly increased K17 immunoreactivity that extended to the basal layer of the epidermis. K16 immunoreactivity was also increased, while K14 showed no change. Total protein extracts were prepared from the dorsal skin of these mice and analyzed to confirm these alterations in keratin expression. Relative to vehicle-treated samples, SF-treated samples exhibited increased levels of K17 and K16, whereas the level of K14 was unaltered. This sustained treatment regimen did not appear to affect skin morphology or alter the rate of apoptosis, in agreement with a previous study involving topical SF treatment at a higher frequency over an 11-week period (Dinkova-Kostova et al., 2006).

To ascertain whether chronic topical application can result in systemic exposure, blood and liver samples were tested for levels of SF and its metabolites, collectively known as dithiocarbamates (DTCs) (Zhang et al., 1996; Ye et al., 2002). The levels of SF and DTCs in blood and liver homogenates were below the sensitivity of the assay. Liver homogenates were also tested for NQO1 activity, and there was no significant difference between control groups (1150 mOD/min/mg in untreated mice; 1053 mOD/min/mg in vehicle-treated mice) and SF-treated mice (1161 mOD/min/mg). Taken together, these results suggest that systemic exposure is unlikely to occur in the context of the treatment regimen used.

Example 4

Optimization of Sulforaphane Treatment Regime for K14 Null Mice

The effectiveness of treatment with sulforaphane (SF) in preventing or reducing skin blistering was tested in K14 null mice. The treatment regimen initially used entailed topical application of 1 µmol SF in jojoba oil (100 µl volume) at P0, P1, and P3. This postnatal treatment regimen reduced cutaneous blistering in several K14 null pups, but the "clinical success" achieved proved variable. Histological analyses revealed that K14-null mice already exhibited a significant amount of "sub-clinical blistering" at birth, that is, prior to the first SF application. In other instances where K14 null mice were successfully rescued, expression of the "rescue" keratin (K16, K17) began prior to birth in basal keratinocytes of the epidermis (Paladini and Coulombe, 1999). SF administered to pregnant mice crosses the placental barrier (Coulombe and Kerns, unpublished data; Noyan-Ashraf et al., 2006), and could conceivably cause an induction of K16/K17 in fetal epidermis at a prenatal stage. Pregnant female mice were given an intraperitoneal (IP) injection of 5 µmol SF, and the embryos were retrieved and their skin and body were separately assayed for levels of SF and DTCs. These analyses provided evidence that K17 is indeed induced in fetal epidermis. Based on these results, the treatment regimen was set as consisting of 3 IP injections of 5 µmol SF administered to the mother every other day during the week prior to delivery, followed by topical application of 1 µmol SF (in 100 µl of jojoba oil) at P0, P1, P3 and P5 post-birth.

These findings established that the SF treatment regimen can be modified to meet the "clinical demands" of the overall phenotype.

Example 5

Sulforaphane Treatment Reduces Cutaneous Blistering in K14 Null Mice

The revised sulforaphane (SF) treatment regimen had a dramatic impact on the appearance and integrity of K14 null mouse skin. K14 null pups could no longer be identified based on their appearance and behavior at P0.5 and even P2.5 At P4.5, many of the K14 null pups showed limited blistering restricted to the front paws. During this early postnatal period, the difference between untreated and SF-treated K14 null pups was indeed dramatic. Whereas nearly all of the untreated K14 null pupa had died by P3 (n=14), 90% of the SF-treated K14 null pups (n=26) were alive and thriving at P4.

Histological analyses were conducted with a special focus on forepaw, which consistently shows very severe skin blistering in K14 null mice. At P2.5, the skin was significantly protected in SF-treated mice relative to untreated K14 null controls. K14 null pups had markedly less sub-clinical blistering of their forepaws, back skin, and snout than control at P0. These data were confirmed by quantification of the surface area of forepaw skin showing blistering in untreated and SF-treated K14 null mice.

Virtually all of the SF-treated K14-null mice developed progressive wasting beyond P4, and most of them died within a day or two. Unlike skin, which remained largely blister-free, the lips and oral mucosa showed the telltale signs of severe blistering. The topical mode of SF delivery during the postnatal phase of the treatment regimen was not effective for maintenance of K16/K17 expression in the oral mucosa, and accordingly this component of the K14 null phenotype was likely responsible for the demise of the mice beyond P4.

Example 6

The Therapeutic Benefit of Sulforaphane Correlates with K17 Induction in Epidermis Sulforaphane (SF) treatment regimen had no obvious impact on mouse epidermal architecture. To further probe into this issue, intact back skin tissue from P2 mice, SF-treated and untreated, was subjected to ultrastructural and immunohistochemical analyses. Phenotypic rescue correlated with the presence of K17 antigens in the basal layer of SF-treated epidermis. These results contrasted with untreated K14 null skin, which showed a spotty distribution of K17 (and K16) restricted to the suprabasal compartment. Early and late differentiation markers, such as K1 and filaggrin, were completely normal in SF-treated K14-null mouse epidermis.

The K14, K16 and K17 genes and proteins are highly conserved between human and mouse at the level of sequence (FIG. 2), tissue distribution, and regulation (McGowan et al., 1998; Coulombe et al., 2004). In particular, these keratins' ability to provide structural support in the epidermis are similar (Paladini and Coulombe, 1999; Kerns et al.). Thus, the data collected from the K14 null mouse model for EBS are directly applicable to the skin of patients suffering from EBS as a result of mutations at the K14 locus. While there are only a few reports describing the equivalent of a K14 null mutation in the human population (Chan et al., 1994; Rugg et al., 1994; Jonkman et al., 1996; El-Ghalbzouri et al., 2003), the present inventors have provided evidence that the SF-dependent induction of K16 and K17 in the basal keratinocytes of human epidermis alleviates the dominant negative impact of missense K14 alleles.

Accordingly, topical application of SF or an Nrf2 inducer is effective in preventing skin blistering in the relevant subset of EBS patients. Studies conducted in our laboratory have shown that SF-induced K17 protein is very long-lived in newborn as well as adult mouse epidermis (Bernot et al., 2005). The data provided above show that, in the mouse, there is no systemic exposure to SF or a pharmacologically active metabolite in the context of the topical treatment regimen devised. These findings indicate that, beyond infancy, EBS patients will achieve a significant preventive benefit from topical application of SF or an Nrf2 inducer twice a week for most body sites and under most conditions. More frequent applications may be needed during the first few months after birth and especially during the neonatal period, when for unknown reasons the EBS clinical symptoms are most pronounced (Fine et al., 1991; 2000).

SF-mediated Induction of K16 and K17, along with its impact on the expression or metabolic and anti-oxidant enzymes and proteins, is also beneficial in the treatment of other conditions in which the skin exhibits fragility as a result of a mutation in a gene encoding a key cytoskeletal component.

It will be apparent to those skilled in the art that various modifications and variations can be made in the methods and compositions of the present invention without departing from the spirit or scope of the invention. Thus, it is intended that the present invention cover the modification and variations of the invention provided they come within the scope of the appended claims and their equivalents.

REFERENCES

Bernot, K. M., Lee, C. H., Coulomb., P. A. 2005. A small surface hydrophobic stripe in the coiled-coil domain of type I keratins mediates tetramer stability. *J Cell Biol* 168 (6): 963-974.

Bianchi, N., DePianto, D., McGowan, K., Gu, C., Coulombe, P. A. 2005. Exploiting the keratin 17 gene promoter to visualize live cells in epithelial appendages of mice, Mol Cell Biol 25: 7249-7259.

Braun, S., Hanselmann, C. Gassmmnn, M. G., auf dem Keller, U., Born-Berelaz, C., Chan, K., Ken, Y. W., and Werner, S. 2002. Nrf2 transcription factor, a novel target of keratinocyte growth factor action which regulates gene expression and Inflammation in the heating skin wound. Mol Cell Biol 22 (15): 5492-5505.

Cao, T., Longlay, M. A., Wang. X. J., Roop, D. R. 2002. An inducible mouse model for epidermolysis bullosa simplex; implications for gene therapy. J Cell Biol 152 (3): 651-656.

Cassidy, A. J., Lane, E. B., McLean, W. H. I. 2002. The human intermediate filament mutation database. http://wwwinterfileorg.

Chan, Y., Anton-Lamprecht, I., Yu. Q. C., Jackal, A. Zabel, B., Ernst, J. P., and Fuchs, E. 1994. A human keratin 14 "knockout": the absence of K14 leads to severe epidermolysis bullosa simplex and a function for an intermediate filament protein. *Genes Dev* 5 (21): 2574-2587.

Cornblatt, B. S., Ye, L., Dinkova-Kostova, A. T., Erb, M., Fahey, J. W., Singh, N. K., Chen, M. S., Stierer, T., Garrett-Meyer, E., Argani, P. Davidson. N. E., Tally, P., Kensler, T. W., and Visvanathan, K. 2007. Preclinical and Clinical Evaluation of Sulforaphane for Chemoprevention in the Breast. *Carcinogenesis*.

Coulombe, P. A., Hutton, M. E., Letai, A., Hebert, A., Paller, A. S., Fuchs, E. 1991. Point mutations in human keratin 14 genes of epidermolysis bullosa simplex patients: genetic and functional analyses. *Cell* 66 (6): 1301-1311.

Coulombe, P. A. and Omary, M. B. 2002. 'Hard' and 'soft' principles defining the structure, function and regulation of keratin intermediate filaments. *Curr Opin Cell Biol* 14 (1): 110-222.

Coulomb., P. A., Tong. X., Mazzalupo, S., Wang, Z., Wong, P. 2004. Great promises yet to be fulfilled: Defining keratin intermediate filament function in vivo. *Eur J Cell Biol* 83 (11-12): 735-746.

Diaakove-Kostova A T, Fahey J W, Wade K L, Jenkins S N, Shapiro T A. Fuchs E J, Kerns M L. Talalay P. 2007. Induction of she Phase 2 Response in Mouse and Human Skin by Sulforaphane-containing Broccoli Sprout Extracts. Cancer Epidemiol Biomarkers Prev. 16 (4): 847-51.

Dinkova-Kostova, A. T., Jenkins, S. N., Fahey, J. W., Ye, L., Wehage, S. L., Liby, K. T., Stephenson, K. K. Wade, K. L., and Talalay, P. 2006. Protection against UV-light-induced skin carcinogenesis in SKH-1 high-risk mice by sulforaphane-containing broccoli sprout extracts. *Cancer Left* 240 (2): 243.252.

Dinkova-Kostova, A. T., Liby, K. T., Stephenson, K. K., Holtzclaw, W. D., Gao, X., Suh, N., Williams, C., Risingsong, R., Honda, T., Gribble, G. W., Sporn, M. B., ad Talalay, P, 2005. Extremely potent triterpenoid inducers of the phase 2 response: correlations of protection against oxidant and inflammatory stress. *Proc Natl Acad Sci USA* 102 (12): 4514-4589.

El Ghalbzouri, A., Jonkman, M., Kempenaar, J., and Ponec, M. 2003. Recessive epidermolysis bullosa simplex phenotype reproduced in vitro: ablation of keratin 14 is partially compensated by keratin 17. *Am J Pathol* 163 (5): 1771-1779.

El Laithy, H. M. ad El-Shabouy, K. M. 2002. The development of Cutina lipogels and gel microemulsion for topical administration of fluconazole. *AAPS PhanmSciTech* 3 (4): B35.

Fahey, J. W. and Talalay, P. 1999. Antioxidant functions of sulforaphane: a potent inducer of Phase II detoxication enzymes. *Food Chem Toxicol* 37 (9-10): 973-979.

Fahey, J. W., Zhang. Y. and Talalay, P. 1997. Broccoli sprouts: an exceptionally rich source of inducers of enzymes that protect against chemical carcinogens. Proc Natl Acad Sci USA 94 (19): 10367-10372.

Fimognari, C., Nusse, M., Cesari, R., Iori, R., Cantelli-Forti, G., and Hrelia, P. 2002. Growth Inhibition, cell-cycle arrest and apoptosis in human T-cell leukemia by the isothiocyanate sulforaphane. *Carcinogenesis* 23 (4): 581-586.

Fine, J. D., Bar, E. A., Briggaman, R. A., Carter, D. M., Eady, R. A., Esterly, N. B., Holbrook, K. A., Hurwitz, S., Johnson, L., Lin, A., et al. 1991. Revised clinical and laboratory criteria for subtypes of inherited epidermolysis bullosa. A consensus report by the Subcommittee on Diagnosis and Classification of the National Epidermolysis Bullosa Registry. *J Am Acad Dermatol* 24 (1): 119-135.

Fine, J. D., Eady, R. A., Bauer, E. A., Briggaman, R A., Bruckner-Tuderman, L., Christiano, A., Heagerty, A., Hintner, H., Jonkman, M. F., McGrath, J., McGuire, J. Moshell, A., Shimizu, H., Tadini, G., Uitto, J. 2000. Revised classification system for inherited epidermolysis bullosa: Report of the second international consensus meeting on diagnosis and classification of epidermolysis bullosa. *J Am Acad Dermatol* 42:1051-1066.

Fuchs, E. 1995. Keratins and the skin. *Ann Rev Cull Dev Biol* 11: 123-153.

Fuchs, E., Cleveland, D. W. 1998. A structural scaffolding of intermediate filaments in health and disease. *Science* 279: 514-519.

Fuchs, E., Weber, K. 1994. Intermediate Filaments: Structure, Dynamics, Function, and Disease. *Ann Rev Biochem* 63: 345-382.

Gamet-Payrastre, L., Li, P., Lumeau, S., Cassar, G., Dupont, M. A., Chevolleau, S., Case, N., Tulllez, J., and Teroc, F. 2000. Sulforaphane, a naturally occurring isothiocyanate, induces cell cycle arrest and apoptosis in HT29 human colon cancer cells. *Cancer Res* 60 (5): 1426-1433.

Gills J J, Jeffery, E H, Matusheski N V, Moon R C, Lantvit D D, Pezzuto J M. 2006. Sulforaphane prevents mouse skin tumorgenesis during the stage of promotion, *Cancer Lett.* 236 (1):72-9.

Gingras, D., Gendron, M., Bolvin, D., Moghrabi, A., Theorat. Y., and Beliveau, R. 2004. Induction of medulloblastoma call apoptosis by sulforaphane, a dietary anticarcinogen from Brassica vegetables. *Cancer Lett* 203 (1): 35-43.

Grachtchouk, M., Mo, R., Yu, S., Zhang, X., Sasaki, H., Hui, C. C., and Dlugosz, A. A. 2000. Basal cell carcinomas in mice overexpressing Gli2 in skin. *Nat Genet* 24 (3): 216-217.

Gross C L, Nealley E W, Nipwoda M T, Smith W J. 2006. Pretreatment of human epidermal keratinocytes with D,L-sulforaphane protects against sulfur mustard cytotoxicity. *Cutan Ocul Toxicol.* 25 (3): 155-63.

Gu, L. H. and Coulombe, P. A. 2007. Keratin function in skin epithelia: a broadening palette with surprising shades. *Curr Opin Cell Biol* 19 (1): 13-23.

Hecht, S. S. 1995. Chemoprevention by isothiocyanates. *J Cell Biochem Supply* 22: 195-209.

Hotlzclaw, W. D., Dinkova-Kostova, A. T., Talalay. P. 2004. Protection against electrophile and oxidative stress by induction of phase 2 genes: The quest for the elusive sensor that responds to inducers. *Adv Enzyme Regul* 44: 335-367.

Iida K, Itoh K, Kumagai Y, Oyasu R, Hattori K, Kawai K, Shimazui T, Akaza H. Yamamoto M (2004). Nrf2 is essential for the chemopreventive efficacy of oltipraz against urinary bladder carcinogenesis. *Cancer Res.* 64: 6424-31.

Irvine, A. D. and McLean, W. H. 1999. Human keratin disease: the increasing spectrum of disease and subtlety of the phenotype-genotype correlation. *Br J Dermatol* 140 (5): 815-828.

Jonkman, M. F., Heeres, K., Pas, H. H., van Luyn, M. J., Elema, J. D., Corden, L. D., Smith, F. J., McLean, W. H, Ramaekers, F. C., Burton, M., and Scheffer, H. 1996. Effects of keratin 14 ablation on the clinical and cellular phenotype in a kindred with recessive epidermolysis bullosa simplex. *J Invest Dermatol* 107 (5): 764-769.

Kerns, M L, DePianto, D, Dinkova-Kostova, A T, Talalay, P. and Coulombe, P A. 2007, Reprogramming of keratin biosynthesis by sulforaphane restores skin integrity in epidermolysis bullosa simplex. PNAS 104 (36): 14460-65.

Keum Y S, Yu S, Chang P P, Yuan X, Kim J H, Xu C, Han J, Agarwal A, Kong A N, 2006. Mechanism of Action of Sulforaphane: Inhibition of p38 Mitogen-Activated Protein Kinase Isoforms Contributing to the induction of Antioxidant Response Element-Mediated Heme Oxygenase-1 in Human Hepatoma HepG2 Cells. *Cancer Res.* 66 (17): 8804-13.

Killeen M E, Englert J A, Stolz D B, Song M, Han Y, Delude R L, Kellum J A, Pink M P, 2006, The phase 2 enzyme inducers othacrynic acid, DL-sulforaphane, and oltipraz inhibit lipopolysaccharide-induced high-mobility group box 1 secretion by RAW 264.7 cells. *J Pharmacol Exp Ther.* 316 (3): 1070-9.

Kim, S., Wong, P., Coulombe, P. A. 2006. A keratin cytoskeletal protein regulates protein synthesis and epithelial cell growth. *Nature* 441 (7091): 362-365.

Lloyd, C., Yu, Q. C., Chang, J., Turksen, K., Degenstein, L., Hutton, E. and Fuchs, E. 1995. The basal keratin network of stratified squamous epithelia: defining K15 function in the absence of K14. J Cell Biol 129 (5): 1329-1344.

McGowan, K. M., Coulombs, P. A. 1998a. The wound repair associated keratins 6, 16, and 17: Insights into the role of intermediate filaments in specifying cytoarchitecture, in *Subcellular Biochemistry: Intermediate Filaments* (ad. J. R. Harris, Herrmann, H.), pp. 141-165, Plenum Publishing Co. London.

McGowan, K. M., Coulombe, P. A, 1998b, Onset of keratin 17 expression coincides with the definition of major epithelial lineages during skin development. *J. Cell Biol.* 143: 469-86.

McGowan, K. M., Tong. X. Colucci-Guyon, E., Langa, P., Babinet, C., and Coulombe, P. A. 2002, Keratin 17 null mice exhibit age- and strain-dependent alopecia. *Genus Dev* 16 (11): 1412-1422.

Misiewicz, I., Skupinska, K., and Kasprzycka-Guttman, T. 2003. Sulforaphane and 2-oxohexyl isothiocyanate induce call growth arrest and apoptosis in L-1210 leukemia and ME-18 melanoma cells. *Oncol Rep* 10 (6); 2045-2050.

Motohashi H, and Yamamoto M. Nrf2-Keap1 defines a physiologically important stress response mechanism. 2004 Trends Mol Med. 10 (11):549-57.

Nelson, W. G. and Sun, T. T. 1983. The 50- and 58-kdalton keratin classes as molecular markers for stratified squamous epithelia: cell culture studies. *J Cell Biol* 97 (1): 244-251.

Noyan-Ashraf, M. H., Wu, L., Wang, R, and Juurlink, B. H. 2006. Dietary approaches to positively Influence fetal determinants of adult health. *Faseb J* 20 (2): 371-373.

Omary, M. B. Coulombe, P. A., McLean, W. H. I. 2004. Intermediate filament proteins and their associated diseases. *N Engl J Med* 33 (20): 2017-2100.

Paladini, R. D., Coulombe, P. A. 1998. Directed expression of keratin 16 to the progenitor basal cells of transgenic mouse skin delays skin maturation. J Cell Biol 142: 1035-1051.

Paladini, R. D., Coulombe, P. A. 1999. The functional diversity of epidermal keratins revealed by the partial rescue of the keratin 14 null phenotype by keratin 16. *J Cell Biol* 146 (5); 1185-1201.

Paladini, R. D., Takahashi, K., Bravo, N. S. Coulombe, P. A. 1996. Onset of re-epithelialization after skin injury correlates with a reorganization of keratin filaments in wound edge keratinocytes: defining a potential role for keratin 16. *J Cell Biol* 32 (3): 381-397.

Peters, B., Kirfel, J., Bussow, H., Vidal, M., Magin, T. M. 2001. Complete cytolysis and neonatal lethality in keratin 5 knockout mice reveal its fundamental role in skin integrity and in epidermolysis bullosa simplex. *Mol Biol Cell* 12 (6): 1775-1789.

Pledgie-Tracy A, Sobolewski M D, Davidson N E. 2007. Sulforaphane induces cell type-specific apoptosis in human breast cancer cell lines. *Mol Cancer Ther.* 6 (3): 1013-21.

Haristoy X, Angioi-Duprez K, Duprez A, Lozniewski A. 2003. Efficacy of sulforaphane in eradicating *Helicobacter pylori* in human gastric xenografts implanted in nude mice. *Antimicrob Agents Chemother.* 47 (12):3982-4.

Prochazka, Z. 1959. Isolation of sulforaphane from hoary cress (*Lepidium draba* L.) Preliminary communication, *Collection of Czechoslovak Chemical Communications* 24, 3606-3610.

Rugg, E. L., McLean. I. W. H., Lane, L. B., Pitera, R., McMillan, J. R., Dopping-Hepenstal, P. J. C., Navsaria, H. A., Leigh, I. M., Eady, R. A. J. 1994. A functional "knockout" of human keratin 14. *Genes Dry* 8: 2563-2573.

von Schmid, H. and Karrer, P. 1948. Synthesis of racemic and optically active forms of sulforaphane. *Helv Chim Acta* 31, 1497-1505.

Shapiro, T. A., Fahey, J. W., Dinkova-Kostova, A. T., Holtzclaw, W. D., Stephenson, K. K., Wade, K. L., Ye, L., and Talalay. P. 2006. Safety, tolerance, and metabolism of broccoli sprout glucosinolates and isothiocyanates: a clinical phase 1 study. *Nutr Cancer* 55 (1): 53-62.

Schweizer, J., Bowdan, P. E., Coulombe, P. A., Langbein, L., Lane, E. B., Magin. T. M., Maltais, L., Omary, M. B., Parry, D. A. Rogers, M. A., Wright, M. W. 2006. New consensus nomenclature for mammalian keratins. *J Cell Biol* 174 (2): 169-174.

Troyanovsky, S. M., R. B. Leube, and W. W. Franke, 1992. Characterization of the human gene encoding cytokeratin 17 and its expression pattern. *Eur J Cell Biol.* 59:127-37.

Wong. P. Domergue. R., Coulombe P. A. 2005. Overcoming functional redundancy to elicit pachyonychia cogenita-like nail lesions in transgenic mice. *Molecular Cellular Biology* 25 (1): 197-205.

Tong, X. Coulombe, P. A. 2006. Keratin 17 regulates hair follicle cycling in a TNFalpha-dependent fashion. *Genes & Dev* 20: 1353-1364.

Xu C, Shen G, Yuan X, Kim J H, Gopalkrishnan A, Keum Y S, Nair S, Kong A N. 2006. ERK and JNK signaling pathways are involved in the regulation of activator protein 1 and cell death elicited by three isothiocyanates in human prostate cancer PC-3 cells. *Carcinogenesis.* 27 (3):437-45.

Ye, L., Dinkova-Kostova, A. T., Wade, K. L., Zhang, Y., Shapiro, T. A., and Talalay, P. 2002. Quantitative determination of dithiocarbamates in human plasma, serum, erythrocytes and urine: pharmacokinetics of broccoli sprout isothiocyanates in humans. *Clin Chim Acta* 316 (1-2): 43-53.

Zhang Y, Kensler T W, Cho C G, Posner G H, Talalay P. 1994. Anticarcinogenic activities of sulforaphane and structurally related synthetic norbornyl isothiocyanates. *Proc Natl Acad Sci USA.* 91 (8):3147-50.

Zhang, Y. and Talalay, P. 1994. Anticarcinogenic activities of organic isothiocyanates: chemistry and mechanisms. *Cancer Res* 54 (7 Suppl): 1976s-1981s.

Zhang, Y., Talalay, P., Cho, C. O., and Posner, G. H. 1992. A major inducer of anticarcinogenic protective enzymes from broccoli: isolation and elucidation of structure. *Proc Marl Acad Sci USA* 89 (6): 2399-2403.

Zhang, Y., Wade, K. L., Prestera, T., and Talalay, P. 1996. Quantitative determination of isothiocyanates, dithiocarbamates, carbon disulfide, and related thiocarbonyl compounds by cyclocondensation with 1,2-benzenedithiol. *Anal Biochem* 239 (2): 160-167.

Zhu M, Zhang Y, Cooper S, Sikorski E, Rohwer J, Bowden G T. 2004. Phase II enzyme inducer, sulforaphane, inhibits UVB-induced AP-1 activation in human keratinocytes by a novel mechanism. *Mol Carcinog.* 41 (3):179-86.

The invention claimed is:

1. A method for treating or preventing skin blistering in a patient in need thereof or at risk of developing skin blistering, comprising administering to the patient a composition comprising a therapeutically effective amount of an Nrf2 inducer.

2. The method of claim 1, wherein the patient suffers from skin blistering.

3. The method of claim 1, wherein the Nrf2 inducer is a phase II enzyme inducer.

4. The method of claim 3, wherein the phase II inducer is an isothiocyanate.

5. The method of claim 4, wherein the phase II enzyme inducer is sulforaphane.

6. The method of claim 4, wherein the phase II enzyme inducer is a sulforaphane synthetic analogue.

7. The method of claim 6, wherein the sulforaphane synthetic analogue is exo-2-acetyl-6-isothiocyanatonorbomane.

8. The method of claim 1, wherein the Nrf2 inducer is keratinocyte growth factor.

9. The method of claim 1, wherein the Nrf2 inducer is oltipraz.

10. The method of claim 1, wherein the Nrf2 inducer is ethacrynic acid.

11. The method of claim 1, wherein the Nrf2 inducer causes the selective induction of K6, K16 or K17 in the keratinocytes in the skin of the patient.

12. The method of claim 1, wherein the composition comprising the NRF2 inducer is topically administered to the patient.

13. The method of claim 12, wherein the amount of Nrf2 inducer in the composition topically administered to the patient is from about 100 nmol/cm2 to about 1 µmol/cm2.

14. The method of claim 12, wherein the composition comprising the Nrf2 inducer is a topical preparation selected from the group consisting of ointment, cream, emulsion, lotion and gel.

15. The method of claim 13, wherein the composition father comprises one or more pharmaceutical, biological or molecular biological active agents.

16. The method of claim 1, wherein the patient is a mammal.

17. The method of claim 16, wherein the mammal is a human.

18. The method of claim 1, wherein the patient suffers from Epidermolysis bullosa simplex.

19. The method of claim 1, wherein the patient suffers from Epidermolysis bullosa simplex-Weber-Cockayne type, Epidermolysis bullosa simplex-Koebner type, Epidermolysis bullosa simplex with mottled pigmentation, Epidermolysis bullosa simplex-Dowling-Meara type, or Epidermolysis bullosa simplex with muscular dystrophy.

20. The method of claim 19, wherein the Epidermolysis bullosa simplex is caused by a mutation at the K14 locus.

21. The method of claim 1, wherein the Nrf2 inducer is a phase II enzyme inducer.

22. The method of claim 21, wherein the phase II inducer is an isothiocyanate.

23. The method of claim 21, wherein the phase II enzyme inducer is sulforaphane.

24. The method of claim 21, wherein the phase II enzyme inducer is a sulforaphane synthetic analogue.

25. The method of claim 24, wherein the sulforaphane synthetic analogue is exo-2-acetyl-6-isothiocyanatonorbornane.

26. The method of claim 1, wherein said skin blistering is a keratin-based skin disease.

27. The method of claim 26, wherein the keratin-based skin disease is selected from the group consisting of epidermolytic hyperkeratosis, ichtyosis bullosa of Siemens, pachyonychia congenita, epidermolytic or non-epidermolytic palmoplantar keratoderma (diffuse or focal) steatocystoma multiplex, Naegeli-Franceschetti4adessohn syndrome and dermatopathia pigmentosa reticularis.

28. The method of claim 26, wherein the disease is caused by a mutation at the K14 locus.

29. The method of claim 26, wherein the Nrf2 inducer is a phase II enzyme inducer.

30. The method of claim 29, wherein the phase II inducer is an isothiocyanate.

31. The method of claim 29, wherein the phase II enzyme inducer is sulforaphane.

32. The method of claim 29, wherein the phase II enzyme inducer is a sulforaphane synthetic analogue.

33. The method of claim 32, wherein the sulforaphane synthetic analogue is exo-2-acetyl-6-isothiocyanatonorbornane.

34. The method of claim 26, wherein the Nrf2 inducer is keratinocyte growth factor.

35. The method of claim 26, wherein the Nrf2 inducer is oltipraz.

36. The method of claim 26, wherein the Nrf2 inducer is ethacrynic acid.

37. The method of claim 26, wherein the Nrf2 inducer causes the selective induction of K6, K16 or K17 in the keratinocytes in the skin of the patient.

38. The method of claim 26, wherein the composition comprising the Nrf2 inducer is topically administered to the patient.

39. The method of claim 38, wherein the amount of Nrf2 inducer in the composition topically administered to the patient is from about 100 nmol to about 1 μmol/cm2.

40. The method of claim 38, wherein the composition comprising the Nrf2 inducer is a topical preparation selected from the group consisting of ointment, cream, emulsion, lotion and gel.

41. The method of claim 39, wherein the composition further comprises one or more pharmaceutical, biological or molecular biological active agents.

42. The method of claim 26, wherein the patient is a mammal.

43. The method of claim 42, wherein the mammal is a human.

44. The method of claim 15, wherein the one or more pharmaceutical, biological or molecular biological active agents comprises jojoba oil.

45. The method of claim 41, wherein the one or more pharmaceutical, biological or molecular biological active agents comprises jojoba oil.

46. The method of claim 1, further comprising identifying a patient with skin blistering or pre-disposed to developing skin blistering.

47. The method of claim 1, wherein the method comprises treating skin blistering in a patient in need thereof comprising administering to the patient a composition comprising a therapeutically effective amount of an Nrf2 inducer.

* * * * *

SEQUENCE LISTING

```
<160> NUMBER OF SEQ ID NOS: 4

<210> SEQ ID NO 1
<211> LENGTH: 433
<212> TYPE: PRT
<213> ORGANISM: Mus musculus

<400> SEQUENCE: 1

Met Thr Thr Thr Ile Arg Gln Phe Thr Ser Ser Ser Ser Ile Lys Gly
```

-continued

```
1               5                   10                  15
Ser Ser Gly Leu Gly Gly Gly Ser Ser Arg Thr Ser Cys Arg Leu Ser
                20                  25                  30
Gly Ser Leu Gly Ala Gly Ser Cys Arg Leu Gly Ser Ala Ser Gly Leu
                35                  40                  45
Gly Ser Ala Leu Gly Ser Asn Ser Tyr Ser Ser Cys Tyr Ser Phe Gly
                50                  55                  60
Thr Gly Ser Gly Tyr Gly Gly Asn Phe Gly Gly Val Asp Gly Leu Leu
65                  70                  75                  80
Ala Gly Gly Glu Lys Ala Thr Met Gln Asn Leu Asn Asp Arg Leu Ala
                85                  90                  95
Ser Tyr Leu Asp Lys Val Arg Ala Leu Glu Glu Ala Asn Thr Glu Leu
                100                 105                 110
Glu Val Lys Ile Arg Asp Trp Tyr Gln Lys Gln Ala Pro Gly Pro Ala
                115                 120                 125
Arg Asp Tyr Ser Ala Tyr Tyr His Thr Ile Glu Asp Leu Lys Asn Lys
                130                 135                 140
Ile Leu Val Ala Thr Val Asp Asn Ala Ser Ile Leu Leu Gln Ile Asp
145                 150                 155                 160
Asn Ala Arg Leu Ala Ala Asp Asp Phe Arg Thr Lys Phe Glu Thr Glu
                165                 170                 175
Gln Ala Leu Arg Met Ser Val Glu Ala Asp Ile Asn Gly Leu Arg Arg
                180                 185                 190
Val Leu Asp Glu Leu Thr Leu Ala Arg Ala Asp Leu Glu Met Gln Ile
                195                 200                 205
Glu Asn Leu Lys Glu Glu Leu Ala Tyr Leu Lys Lys Asn His Glu Glu
                210                 215                 220
Glu Met Asn Ala Leu Arg Gly Gln Val Gly Gly Glu Ile Asn Val Glu
225                 230                 235                 240
Met Asp Ala Ala Pro Gly Val Asp Leu Ser Arg Ile Leu Ser Glu Met
                245                 250                 255
Arg Asp Gln Tyr Glu Lys Met Ala Glu Lys Asn Arg Lys Asp Ala Glu
                260                 265                 270
Asp Trp Phe Phe Ser Lys Thr Glu Glu Leu Asn Arg Glu Val Ala Thr
                275                 280                 285
Asn Ser Glu Leu Val Gln Ser Gly Lys Ser Glu Ile Ser Glu Leu Arg
                290                 295                 300
Arg Thr Met Gln Ala Leu Glu Ile Glu Leu Gln Ser Gln Leu Ser Met
305                 310                 315                 320
Lys Ala Ser Leu Glu Gly Ser Leu Ala Glu Thr Glu Asn Arg Tyr Cys
                325                 330                 335
Val Gln Leu Ser Gln Ile Gln Gly Leu Ile Gly Ser Val Glu Glu Gln
                340                 345                 350
Leu Ala Gln Leu Arg Cys Glu Met Glu Gln Gln Asn Gln Glu Tyr Lys
                355                 360                 365
Ile Leu Leu Asp Val Lys Thr Arg Leu Glu Gln Glu Ile Ala Thr Tyr
                370                 375                 380
Arg Arg Leu Leu Glu Gly Glu Asp Ala His Leu Thr Gln Tyr Lys Pro
385                 390                 395                 400
Lys Glu Pro Val Thr Thr Arg Gln Val Arg Thr Ile Val Glu Glu Val
                405                 410                 415
Gln Asp Gly Lys Val Ile Ser Ser Arg Glu Gln Val His Gln Thr Thr
                420                 425                 430
```

Arg

<210> SEQ ID NO 2
<211> LENGTH: 432
<212> TYPE: PRT
<213> ORGANISM: Homo sapiens

<400> SEQUENCE: 2

```
Met Thr Thr Ser Ile Arg Gln Phe Thr Ser Ser Ser Ile Lys Gly
 1               5                  10                  15

Ser Ser Gly Leu Gly Gly Gly Ser Ser Arg Thr Ser Cys Arg Leu Ser
                20                  25                  30

Gly Gly Leu Gly Ala Gly Ser Cys Arg Leu Gly Ser Ala Gly Gly Leu
                35                  40                  45

Gly Ser Thr Leu Gly Gly Ser Ser Tyr Ser Ser Cys Tyr Ser Phe Gly
        50                  55                  60

Ser Gly Gly Gly Tyr Gly Ser Ser Phe Gly Gly Val Asp Gly Leu Leu
65                  70                  75                  80

Ala Gly Gly Glu Lys Ala Thr Met Gln Asn Leu Asn Asp Arg Leu Ala
                85                  90                  95

Ser Tyr Leu Asp Lys Val Arg Ala Leu Glu Ala Asn Thr Glu Leu
                100                 105                 110

Glu Val Lys Ile Arg Asp Trp Tyr Gln Arg Gln Ala Pro Gly Pro Ala
                115                 120                 125

Arg Asp Tyr Ser Gln Tyr Tyr Arg Thr Ile Glu Glu Leu Gln Asn Lys
        130                 135                 140

Ile Leu Thr Ala Thr Val Asp Asn Ala Asn Ile Leu Leu Gln Ile Asp
145                 150                 155                 160

Asn Ala Arg Leu Ala Ala Asp Asp Phe Arg Thr Lys Phe Glu Thr Glu
                165                 170                 175

Gln Ala Leu Arg Leu Ser Val Glu Ala Asp Ile Asn Gly Leu Arg Arg
                180                 185                 190

Val Leu Asp Glu Leu Thr Leu Ala Arg Ala Asp Leu Glu Met Gln Ile
                195                 200                 205

Glu Asn Leu Lys Glu Glu Leu Ala Tyr Leu Lys Lys Asn His Glu Glu
        210                 215                 220

Glu Met Asn Ala Leu Arg Gly Gln Val Gly Gly Glu Ile Asn Val Glu
225                 230                 235                 240

Met Asp Ala Ala Pro Gly Val Asp Leu Ser Arg Ile Leu Asn Glu Met
                245                 250                 255

Arg Asp Gln Tyr Glu Lys Met Ala Glu Lys Asn Arg Lys Asp Ala Glu
                260                 265                 270

Asp Trp Phe Phe Ser Lys Thr Glu Glu Leu Asn Arg Glu Val Ala Thr
                275                 280                 285

Asn Ser Glu Leu Val Gln Ser Gly Lys Ser Glu Ile Ser Glu Leu Arg
        290                 295                 300

Arg Thr Met Gln Ala Leu Glu Ile Glu Leu Gln Ser Gln Leu Ser Met
305                 310                 315                 320

Lys Ala Ser Leu Glu Gly Asn Leu Ala Glu Thr Glu Asn Arg Tyr Cys
                325                 330                 335

Val Gln Leu Ser Gln Ile Gln Gly Leu Ile Gly Ser Val Glu Glu Gln
                340                 345                 350

Leu Ala Gln Leu Arg Cys Glu Met Glu Gln Gln Asn Gln Glu Tyr Lys
                355                 360                 365
```

```
Ile Leu Leu Asp Val Lys Thr Arg Leu Glu Gln Glu Ile Ala Thr Tyr
    370                 375                 380

Arg Arg Leu Leu Glu Gly Glu Asp Ala His Leu Thr Gln Tyr Lys Lys
385                 390                 395                 400

Glu Pro Val Thr Thr Arg Gln Val Arg Thr Ile Val Glu Glu Val Gln
                405                 410                 415

Asp Gly Lys Val Ile Ser Ser Arg Glu Gln Val His Gln Thr Thr Arg
                420                 425                 430

<210> SEQ ID NO 3
<211> LENGTH: 472
<212> TYPE: PRT
<213> ORGANISM: Homo sapiens

<400> SEQUENCE: 3

Met Thr Thr Cys Ser Arg Gln Phe Thr Ser Ser Ser Met Lys Gly
1               5                   10                  15

Ser Cys Gly Ile Gly Gly Gly Ile Gly Ala Gly Ser Ser Arg Ile Ser
                20                  25                  30

Ser Val Leu Ala Gly Gly Ser Cys Arg Ala Pro Asn Thr Tyr Gly Gly
                35                  40                  45

Gly Leu Ser Val Ser Ser Ser Arg Phe Ser Ser Gly Gly Ala Tyr Gly
        50                  55                  60

Leu Gly Gly Gly Tyr Gly Gly Phe Ser Ser Ser Ser Ser Ser Phe
65                  70                  75                  80

Gly Ser Gly Phe Gly Gly Gly Tyr Gly Gly Gly Leu Gly Ala Gly Leu
                85                  90                  95

Gly Gly Gly Phe Gly Gly Gly Phe Ala Gly Gly Asp Gly Leu Leu Val
                100                 105                 110

Gly Ser Glu Lys Val Thr Met Gln Asn Leu Asn Asp Arg Leu Ala Ser
            115                 120                 125

Tyr Leu Asp Lys Val Arg Ala Leu Glu Glu Ala Asn Ala Asp Leu Glu
    130                 135                 140

Val Lys Ile Arg Asp Trp Tyr Gln Arg Gln Arg Pro Ala Glu Ile Lys
145                 150                 155                 160

Asp Tyr Ser Pro Tyr Phe Lys Thr Ile Glu Asp Leu Arg Asn Lys Ile
                165                 170                 175

Leu Thr Ala Thr Val Asp Asn Ala Asn Val Leu Leu Gln Ile Asp Asn
                180                 185                 190

Ala Arg Leu Ala Ala Asp Asp Phe Arg Thr Lys Tyr Glu Thr Glu Leu
            195                 200                 205

Asn Leu Arg Met Ser Val Glu Ala Asp Ile Asn Gly Leu Arg Arg Val
    210                 215                 220

Leu Asp Glu Leu Thr Leu Ala Arg Ala Asp Leu Glu Met Gln Ile Glu
225                 230                 235                 240

Ser Leu Lys Glu Glu Leu Ala Tyr Leu Lys Lys Asn His Glu Glu Glu
                245                 250                 255

Met Asn Ala Leu Arg Gly Gln Val Gly Gly Asp Val Asn Val Glu Met
                260                 265                 270

Asp Ala Ala Pro Gly Val Asp Leu Ser Arg Ile Leu Asn Glu Met Arg
            275                 280                 285

Asp Gln Tyr Glu Lys Met Ala Glu Lys Asn Arg Lys Asp Ala Glu Glu
    290                 295                 300

Trp Phe Phe Thr Lys Thr Glu Glu Leu Asn Arg Glu Val Ala Thr Asn
```

```
              305                 310                 315                 320
Ser Glu Leu Val Gln Ser Gly Lys Ser Glu Ile Ser Glu Leu Arg Arg
                  325                 330                 335

Thr Met Gln Asn Leu Glu Ile Glu Leu Gln Ser Gln Leu Ser Met Lys
                  340                 345                 350

Ala Ser Leu Glu Asn Ser Leu Glu Glu Thr Lys Gly Arg Tyr Cys Met
                  355                 360                 365

Gln Leu Ala Gln Ile Gln Glu Met Ile Gly Ser Val Glu Glu Gln Leu
                  370                 375                 380

Ala Gln Leu Arg Cys Glu Met Glu Gln Gln Asn Gln Glu Tyr Lys Ile
385                 390                 395                 400

Leu Leu Asp Val Lys Thr Arg Leu Glu Gln Glu Ile Ala Thr Tyr Arg
                  405                 410                 415

Arg Leu Leu Glu Gly Glu Asp Ala His Leu Ser Ser Ser Gly Phe Ser
                  420                 425                 430

Ser Gly Ser Gln Ser Ser Arg Asp Val Thr Ser Ser Ser Arg Gln Ile
                  435                 440                 445

Arg Thr Lys Val Met Asp Val His Asp Gly Lys Val Val Ser Thr His
                  450                 455                 460

Glu Gln Val Leu Arg Thr Lys Asn
465                 470

<210> SEQ ID NO 4
<211> LENGTH: 473
<212> TYPE: PRT
<213> ORGANISM: Homo sapiens

<400> SEQUENCE: 4

Met Ala Thr Cys Ser Arg Gln Phe Thr Ser Ser Ser Ser Met Lys Gly
1               5                   10                  15

Ser Cys Gly Ile Gly Gly Gly Ile Gly Gly Gly Ser Ser Arg Ile Ser
                  20                  25                  30

Ser Val Leu Ala Gly Gly Ser Cys Arg Ala Pro Ser Thr Tyr Gly Gly
                  35                  40                  45

Gly Leu Ser Val Ser Ser Arg Phe Ser Ser Gly Ala Cys Gly Leu
                  50                  55                  60

Gly Gly Gly Tyr Gly Gly Gly Phe Ser Ser Ser Ser Ser Phe Gly Ser
65                  70                  75                  80

Gly Phe Gly Gly Gly Tyr Gly Gly Leu Gly Ala Gly Phe Gly Gly
                  85                  90                  95

Gly Leu Gly Ala Gly Phe Gly Gly Phe Ala Gly Gly Asp Gly Leu
                  100                 105                 110

Leu Val Gly Ser Glu Lys Val Thr Met Gln Asn Leu Asn Asp Arg Leu
                  115                 120                 125

Ala Ser Tyr Leu Asp Lys Val Arg Ala Leu Glu Glu Ala Asn Ala Asp
                  130                 135                 140

Leu Glu Val Lys Ile Arg Asp Trp Tyr Gln Arg Gln Arg Pro Ser Glu
145                 150                 155                 160

Ile Lys Asp Tyr Ser Pro Tyr Phe Lys Thr Ile Glu Asp Leu Arg Asn
                  165                 170                 175

Lys Ile Ile Ala Ala Thr Ile Glu Asn Ala Gln Pro Ile Leu Gln Ile
                  180                 185                 190

Asp Asn Ala Arg Leu Ala Ala Asp Asp Phe Arg Thr Lys Tyr Glu His
                  195                 200                 205
```

```
Glu Leu Ala Leu Arg Gln Thr Val Glu Ala Asp Val Asn Gly Leu Arg
    210                 215                 220
Arg Val Leu Asp Glu Leu Thr Leu Ala Arg Thr Asp Leu Glu Met Gln
225                 230                 235                 240
Ile Glu Gly Leu Lys Glu Glu Leu Ala Tyr Leu Arg Lys Asn His Glu
            245                 250                 255
Glu Glu Met Leu Ala Leu Arg Gly Gln Thr Gly Gly Asp Val Asn Val
            260                 265                 270
Glu Met Asp Ala Ala Pro Gly Val Asp Leu Ser Arg Ile Leu Asn Glu
            275                 280                 285
Met Arg Asp Gln Tyr Glu Gln Met Ala Glu Lys Asn Arg Arg Asp Ala
    290                 295                 300
Glu Thr Trp Phe Leu Ser Lys Thr Glu Glu Leu Asn Lys Glu Val Ala
305                 310                 315                 320
Ser Asn Ser Glu Leu Val Gln Ser Ser Arg Ser Glu Val Thr Glu Leu
            325                 330                 335
Arg Arg Val Leu Gln Gly Leu Glu Ile Glu Leu Gln Ser Gln Leu Ser
            340                 345                 350
Met Lys Ala Ser Leu Glu Asn Ser Leu Glu Glu Thr Lys Gly Arg Tyr
            355                 360                 365
Cys Met Gln Leu Ser Gln Ile Gln Gly Leu Ile Gly Ser Val Glu Glu
    370                 375                 380
Gln Leu Ala Gln Leu Arg Cys Glu Met Glu Gln Gln Ser Gln Glu Tyr
385                 390                 395                 400
Gln Ile Leu Leu Asp Val Lys Thr Arg Leu Glu Gln Glu Ile Ala Thr
            405                 410                 415
Tyr Arg Arg Leu Leu Glu Gly Glu Asp Ala His Leu Ser Ser Gln Gln
            420                 425                 430
Ala Ser Gly Gln Ser Tyr Ser Ser Arg Glu Val Phe Thr Ser Ser Ser
            435                 440                 445
Ser Ser Ser Ser Arg Gln Thr Arg Pro Ile Leu Lys Glu Gln Ser Ser
    450                 455                 460
Ser Ser Phe Ser Gln Gly Gln Ser Ser
465                 470
```